(12) United States Patent
Sjoede et al.

(10) Patent No.: US 9,193,982 B2
(45) Date of Patent: Nov. 24, 2015

(54) ENZYMATIC HYDROLYSIS OF CELLULOSE

(75) Inventors: Anders Sjoede, Sarpsborg (NO);
Anders Froelander, Sarpsborg (NO);
Martin Lersch, Sarpsborg (NO);
Gudbrand Roedsrud, Sarpsborg (NO);
Kristin Hals, Sarpsborg (NO); Anne Mari Kloeften, Sarpsborg (NO);
Lennart Delin, Skaerholmen (SE); Mats H Johansson, Norrköping (SE)

(73) Assignee: BORREGAARD AS, Sarpsborg (NO)

( * ) Notice: Subject to any disclaimer, the term of this patent is extended or adjusted under 35 U.S.C. 154(b) by 80 days.

(21) Appl. No.: 13/704,968

(22) PCT Filed: Jun. 16, 2011

(86) PCT No.: PCT/EP2011/002974
§ 371 (c)(1),
(2), (4) Date: May 3, 2013

(87) PCT Pub. No.: WO2011/157427
PCT Pub. Date: Dec. 22, 2011

(65) Prior Publication Data
US 2013/0217074 A1   Aug. 22, 2013

(30) Foreign Application Priority Data

Jun. 17, 2010   (EP) .................................... 10006308

(51) Int. Cl.
| | |
|---|---|
| *C12P 19/14* | (2006.01) |
| *C12P 5/00* | (2006.01) |
| *C08H 7/00* | (2011.01) |
| *C12M 1/00* | (2006.01) |
| *C12N 1/22* | (2006.01) |
| *C12P 7/10* | (2006.01) |
| *C12P 11/00* | (2006.01) |
| *C12P 17/16* | (2006.01) |
| *C12P 19/02* | (2006.01) |
| *C13K 1/02* | (2006.01) |
| *C13K 13/00* | (2006.01) |
| *C08H 8/00* | (2010.01) |
| *C10L 1/02* | (2006.01) |

(52) U.S. Cl.
CPC . *C12P 19/14* (2013.01); *C08H 6/00* (2013.01); *C08H 8/00* (2013.01); *C10L 1/02* (2013.01); *C12M 45/06* (2013.01); *C12N 1/22* (2013.01); *C12P 7/10* (2013.01); *C12P 11/00* (2013.01); *C12P 17/162* (2013.01); *C12P 19/02* (2013.01); *C13K 1/02* (2013.01); *C13K 13/002* (2013.01); *C10G 2300/1014* (2013.01); *C10G 2300/302* (2013.01); *Y02E 50/16* (2013.01); *Y02E 50/17* (2013.01)

(58) Field of Classification Search
None
See application file for complete search history.

(56) References Cited

U.S. PATENT DOCUMENTS

2009/0209009 A1   8/2009   Tolan et al.

FOREIGN PATENT DOCUMENTS

| WO | WO 2009/140674 A2 | 11/2009 |
| WO | WO 2010/078930 A2 | 7/2010 |
| WO | WO 2010/113130 A2 | 10/2010 |

OTHER PUBLICATIONS

Hodge et al., Applied Biochem Biotechnol., 2009, vol. 152, p. 88-107, (published online on May 2008).*
Pimenova et al., Applied Biochemistry and Biotechnology, 2003, vol. 105-108, p. 383-392.*
Dasari et al., Applied Biochemistry and Biotechnology, 2007, vol. 136-140, p. 289-299.*
Zhu et al., Bioresource Technology, 2009, vol. 100, p. 2411-2418.*
Brethauer and Wyman: "Review: Continuous Hydrolysis and Fermentation for Cellulosic Ethanol Production," Bioresource Technology, 2010, vol. 101, p. 4862-4874.
Fan et al: "Conversion of Paper Sludge to Ethanol in a Semicontinous Solids-Fed Reactor," Bioprocess Biosyst Eng, 2003, vol. 26, p. 93-101.
Gan et al: "Analysis of Process Integration and Intensification of Enzymatic Cellulose Hydrolysis in a Membrane Bioreactor," J. Chemical Technology and Biotechnology, vol. 80, 2005, p. 688-698.
Ghose and Kostick: "A Model for Continuous Enzymatic Saccharification of Cellulose with Simultaneous Removal of Glucose Syrup," Biotechnology and Bioengineering, 1970, vol. XII, p. 921-946.
Ghose: "Continuous Enzymatic Sacharification of Cellulose with Culture Filtrates of Trichoderma viride QM 6a", Biotechnology and Bioengineering, vol. XI, 1969, p. 239-261.
Martin et al: "Dilute Sulfuric Acid Pretreatment of Agricultural and Agro-Industrial Residues for Ethanol Production," Applied Biochemistry and Biotechnology, Vo. 136-140, 2007 p. 339-352.

* cited by examiner

*Primary Examiner* — Kade Ariani
(74) *Attorney, Agent, or Firm* — Arnold & Porter LLP; Todd A. Lorenz

(57) ABSTRACT

The present invention relates to a continuous process for the enzymatic hydrolysis of cellulosic biomass and to an apparatus for conducting said process. According to the present invention, a steady state is achieved in a reactor in regard to the hydrolysis reaction. Therein, cellulosic biomass of a high total solids content (preferably 10% or higher, further preferably between 15 and 30%) is continually added to said reactor, while at least partially hydrolyzed cellulosic biomass is continually removed from said reactor. The steady state is adjusted, i.e. the amount of cellulosic biomass added and the amount of at least partially hydrolyzed cellulosic biomass removed is adjusted, so that the retention time of a given portion of added cellulosic biomass in the reactor is longer than its "liquefaction time", i.e. the time period required to transform a solid slurry into a pumpable liquid during hydrolysis, i.e. the time required to lower the viscosity of the slurry to a value, which is acceptable for further processing.

32 Claims, 6 Drawing Sheets

ENZYMATIC HYDROLYSIS OF CELLULOSE

SUMMARY OF THE INVENTION

The present invention relates to a continuous process for the enzymatic hydrolysis of cellulosic biomass. The improved hydrolysis according to the present invention is of particular use in the overall biomass conversion for cellulose, i.e. the process of converting cellulosic biomass into useful chemicals or commodities, for example biofuels.

In one embodiment, the present invention relates to a process for the continuous hydrolysis of cellulosic biomass comprising at least the following steps:

(P) providing at least one reactor, which can be operated at steady state;

(A) adding a predetermined amount of cellulosic biomass to said reactor, wherein said cellulosic biomass has a solid content of at least 10%, preferably at least 15%, preferably at least 20%, preferably at least 25%, further preferably at least 30%; further preferably 10% to 45%, further preferably 15% to 45%, further preferably 20% to 40% or 15% to 30%;

(A') adding a predetermined amount of enzymes to said reactor;

(E) performing at least a partial enzymatic hydrolysis of the cellulosic biomass in said reactor.

In said process, a steady state is achieved, in which cellulosic biomass is continually added to said reactor, while at least partially hydrolyzed cellulosic biomass is continually removed from said reactor, wherein said at least partially hydrolyzed cellulosic biomass that is continually removed has a viscosity, as measured in a Physica MCR 101 rheometer in a cup with a stirrer (FL 100/6 W), of not more than 25 Pas (Pascal seconds), preferably not more than 10 Pas, preferably not more than 5 Pas, further preferably not more than 3 Pas, further preferably not more than 1 Pas.

The viscosity is measured at standard conditions (20° C., 1 bar). The person skilled in the art will take further information on how to measure said viscosity from the Example given in the present application.

Preferably, in said steady state, said viscosity remains essentially constant or remains essentially below any of the above-disclosed values for the viscosity over an extended period of time, for example over the course of 2 hours, 4 hour, 6 hours, 12 hours or more.

The purpose of establishing a steady state in said reactor is to allow for the hydrolysis of cellulosic biomass having a comparatively high solid content. It is desirable to run enzymatic hydrolysis at high solids loadings, preferably 10% total solids content ("TS") or higher, in particular from an environmental and economical perspective, as this reduces water and energy consumption as well as equipment investment costs. However, one of the challenges of hydrolyzing cellulosic biomass of a high solid content is to achieve sufficient mixing given the high viscosity of the slurry with the high solids content. Conventionally, in particular in the batch processes known from the art, mixing is only possible using energy demanding and complex design machinery.

According to the present invention, in said reactor, a hydrolysis reaction in the steady state is achieved. Therein, cellulosic biomass of a high total solids content (preferably 10% or higher, further preferably between 15 and 40%) is continually added to said reactor, while at least partially hydrolyzed cellulosic biomass is continually removed from said reactor. The steady state is adjusted, i.e. the amount of cellulosic biomass added and the amount of at least partially hydrolyzed cellulosic biomass removed is adjusted, so that the average retention time of cellulosic biomass in the reactor is longer than the respective average "liquefaction time", i.e. the time period required to transform a solid slurry into a pumpable liquid during hydrolysis, i.e. the time to required to lower the viscosity of the slurry to a value, which is acceptable for further processing.

In accordance with the present invention, this "liquefaction time" is suitably described by the viscosity of the at least partially hydrolyzed cellulosic biomass that is continually removed from the reactor. Said viscosity, as measured in a Physica MCR 101 rheometer in a cup with a stirrer (FL 100/6 W), is not more than 25 Pas (Pascal seconds), preferably not more than 10 Pas, preferably not more than 5 Pas, further preferably not more than 3 Pas, further preferably not more than 1 Pas.

In a preferred embodiment, according to which the glucose yield of the overall process is increased, the process for the continuous hydrolysis of cellulosic biomass is implemented in a cascade of at least two reactors, i.e. step (P) is:

(P) providing a cascade of at least two reactors, which can be operated at steady state In a preferred embodiment, said process for the continuous hydrolysis of cellulosic biomass at least comprises the following steps:

(P) providing a cascade of at least two reactors, which can be operated at steady state;

(A) adding a predetermined amount of cellulosic biomass to a first reactor, wherein said cellulosic biomass has a solid content of at least 10%, preferably at least 15%, preferably at least 20%, preferably at least 25%, further preferably at least 30%, further preferably 10% to 45%, further preferably 15% to 45%, further preferably 20% to 40% or 15% to 30%;

(A') adding a predetermined amount of enzymes to said first reactor (E) performing partial enzymatic hydrolysis of the cellulosic biomass in said first reactor, (T) continually removing partially hydrolyzed cellulosic biomass from step (E1), which has a viscosity, as measured in a Physica MCR 101 rheometer in a cup with a stirrer (FL 100/6 W), of not more than 25 Pas (Pascal seconds), preferably not more than 10 Pas, preferably not more than 5 Pas, further preferably not more than 3 Pas, further preferably not more than 1 Pas, and transferring the same into a second reactor, which can be operated at steady state;

(E') performing further enzymatic hydrolysis on the partially hydrolyzed cellulosic biomass from step (E) in said second reactor.

BACKGROUND

Prior Art

As is generally accepted, the resources for petroleum-based chemicals and for petroleum used as (fossil) fuel are limited. One presently used alternative resource is "biofuel" as obtained from biomass. Various sources of biomass may be used.

"First-generation biofuels" are biofuels made from sugar, starch, vegetable oil, or animal fats using conventional technology. Exemplary basic feedstock for the production of first generation biofuels are seeds or grains such as wheat, which yield starch that is hydrolyzed and fermented into bioethanol, or sunflower seeds, which are pressed to yield vegetable oil that can be transformed into biodiesel. However, these feedstock could instead enter the animal or human food chain. Therefore, first generation biofuels have been criticized for diverting food away from the human food chain, leading to food shortages and price increases.

By contrast, "second generation biofuel" can be produced sustainably by using biomass comprised of the residual non-food (i.e. non digestible) parts of current crops, such as stems, leaves, bagasse (sugarcane fiber residue), husks etc. that are left behind once the food crop has been extracted, as well as other feedstock that is not used for food purposes (non food crops), such as wood, annual plants and cereals that comprise little grain, and also industry waste such as sawdust, skins and pulp from fruit pressing, wine processing etc.

An important step in the overall biomass conversion for this second generation biofuel is the hydrolysis of untreated or pretreated cellulosic biomass into smaller units. In said hydrolysis step, the cellulose chains are broken by means of breaking at least one β-1-4-glucosidic bond.

More specifically, cellulose is an insoluble linear polymer of repeating glucan units linked by β-1-4-glucosidic bonds. In water, cellulose is typically hydrolyzed by attack of the electrophilic hydrogen of the water molecule on the glycosidic bond. In cellulose chains, each glucose unit has the potential to form three hydrogen bonds with monomers in adjacent chains, resulting in a stable crystalline structure, which is not easily hydrolyzed. The rate of the hydrolysis reaction can be increased by use of elevated temperatures and pressures or can be catalyzed by dilute or concentrated acid or by enzymes (as is the case in the present invention).

On the industrial scale, it is of particular interest to hydrolyze cellulosic biomass with a high solids content. Conventionally, cellulosic biomass having a high solids content is hydrolyzed using excessive hydrolysis times, often spanning 5-7 days, sometimes employing combined setups where hydrolysis and fermentation are performed simultaneously.

US 2009/0209009 relates to the enzymatic hydrolysis of cellulose and discloses that the cost of enzymes can be reduced by introducing a cellulose binding domain onto one of the enzyme components needed for cellulose degradation, namely beta-glucosidase. To achieve this, specific binding agents are needed. This binding agent allows the enzyme to bind to cellulose for convenient recycling. Furthermore, the hydrolysis reaction is performed in dedicated solids retaining reactors, wherein the solids have a retention time which is longer than that of the liquid.

WO 2009/14067 describes a feed batch process with separation of solids and dilution of the substrate to be able to handle high amounts of total suspended solids (TSS) in the reactor.

An article by Brethauer, S.; Wyman, C. E. "Review: Continuous hydrolysis and fermentation for cellulosic ethanol production" *Biores. Technol.* 2010, 4862 discusses batch vs. continuous hydrolysis and fermentation process in general terms, but with emphasis on fermentation. Advantages mentioned include reduced vessel down time for cleaning and filling which translates into an increased volumetric productivity, smaller reactors, lower capital investments, and ease of control at steady state. The data presented in the paper are from continuous fermentation experiments.

An article by Fan, Z. L.; South, C.; Lyford, K.; Munsie, J.; van Walsum, P.; Lynd, L. R. "Conversion of paper sludge to ethanol in a semi continuous solids-fed reactor" *Bioprocess Biosyst. Eng.* 2003, 93 describes a semi-continuous reactor where paper sludge is fed at certain intervals to a reactor running a SSF (=simultaneous saccharification and fermentation). The authors observe that by decreasing the feeding frequency (feed additions per residence time), the cellulase loading can be decreased.

In light of the prior art as discussed above, one object of the present invention is to provide a process for the enzymatic hydrolysis of cellulosic biomass, in which a comparatively high solid content cellulosic biomass can be hydrolyzed under industrial-scale conditions while minimizing (investment and operation) costs.

This object (and others) is/are solved by the following process for the continuous hydrolysis of cellulosic biomass comprising at least the following steps:

(P) providing at least one reactor, which can be operated at steady state;

(A) adding a predetermined amount of cellulosic biomass to said reactor, wherein said cellulosic biomass has a solid content of at least 10%, preferably at least 15%, preferably at least 20%, preferably at least 25%, further preferably at least 30%; further preferably 10% to 45%, further preferably 15% to 45%, further preferably 20% to 40% or 15% to 30%;

(A') adding a predetermined amount of enzymes to said reactor;

(E) performing at least a partial enzymatic hydrolysis of the cellulosic biomass in said reactor, wherein, a steady state is achieved, in which cellulosic biomass is continually added to said reactor, while at least partially hydrolyzed cellulosic biomass is continually removed from said reactor, wherein said at least partially hydrolyzed cellulosic biomass that is continually removed has a viscosity, as measured in a Physica MCR 101 rheometer in a cup with a stirrer (FL 100/6 W), of not more than 25 Pas (Pascal seconds), preferably not more than 10 Pas, preferably not more than 5 Pas, further preferably not more than 3 Pas, further preferably not more than 1 Pas.

Therein, and throughout the entire description of the present invention, the term "solid content" (also known to the person skilled in the art as "TS" or "Total Solids") denotes the ratio between the weight of a sample after it has been dried at 105° C. for 16 h, and the weight of the same sample of prior to said drying.

Correspondingly, the term "TDS" or "Total Dissolved Solids" as used throughout the present application denotes the ratio between the weight of the dried (105° C. for 16 h) filtrate resulting from a sample after it has been filtered and the weight of the same sample prior to said filtering and drying.

The term TSS" or "Total Suspended Solids" denotes the ratio between the weight of the dried (105° C. for 16 h) filter cake resulting from a sample after it has been filtered and the weight of the same sample prior to said filtering and drying. Hence, the connection between these measures is TS=TDS+TSS.

By implementing the continuous process according to the present invention, i.e. by means of establishing a steady state and a defined viscosity regime, the problems based on high initial viscosity and complex reactor design are solved. In particular, the present invention solves the problem of performing a commercially viable enzymatic hydrolysis at a high solids loading, while keeping the viscosity in the reactor low. The present invention allows to run the enzymatic hydrolysis at a high total solids content and at a low total suspended solids ("TSS") content as a continuous process with or without recycling of enzymes.

No special stirring of the reactor is required since there is no problem with high TSS. As a consequence, conventional CSTRs (continuously stirred tank reactors) can be used in for the process of the present invention. Therefore, preferably, the (at least one) reactor used in the process according to the present invention is a continuously stirred reactor, further preferably a continually stirred tank reactor.

A further embodiment that solves the above-recited object(s) also increases the glucose yield of the overall process. Therein, the process for the continuous hydrolysis of cellulosic biomass according to the present invention, in particular step (P) is implemented in a cascade of at least two reactors.

There is no limit in regard to the maximum number of reactors. The number of reactors operated in a cascade (i.e. operated sequentially) essentially depends on the desired glucose yield.

In a preferred aspect of the present invention, the amount of enzymes required in the overall process is reduced by at least 30%, preferably at least 40% by means of including a recycling loop, in which the enzymes are recycled. Therein, the hydrolysate, i.e. the liquid phase comprising the hydrolyzed cellulose and enzymes, from the (last) reactor is subjected to a separation step, wherein the non-hydrolyzed solids are separated from the hydrolysate still containing enzymes. Said liquid hydrolyzate is then mixed with non-hydrolyzed ("fresh") cellulosic biomass, which is then introduced into the (first) hydrolysis reactor.

DETAILED DESCRIPTION OF THE INVENTION

Figure 1:
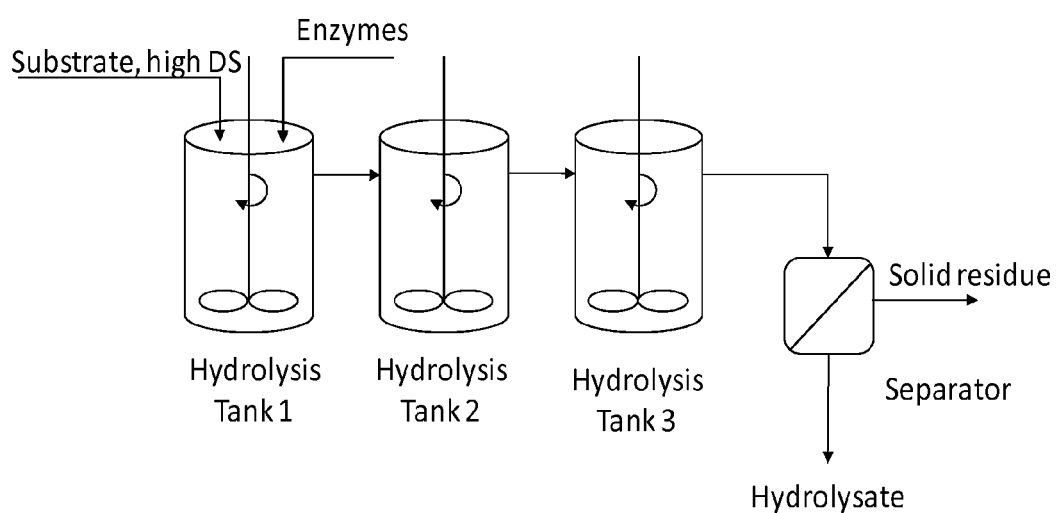
FIG. 1 shows a continuous reactor operated according to the process of the present invention with an optional subsequent cascade of further reactors.

The present invention relates to the hydrolysis of cellulosic biomass. No restrictions exist in regard to the type or composition of the cellulosic biomass other than that said biomass comprises cellulose. According to one suitable definition, "biomass" is the total mass of (previously) living matter, in particular organic matter, within a given unit of environmental area, preferably plant material, vegetation, or agricultural waste used as a fuel or energy source. The fact that "previously" living biomass is also included as "cellulosic biomass" entails that recycled cellulosic materials, in particular recycled cotton materials and/or recycled paper-based products or other conceivable cellulose-based recycled materials, are also included. Any mixture of recycled cellulosic materials, such as recycled paper products, with any other type of cellulosic biomass is also included.

According to a preferred embodiment, said cellulosic biomass comprises more than 30% of cellulose (% by weight, based on the overall mass), preferably more than 50% cellulose, preferably more than 70% cellulose. Therein, the term "cellulose" also comprises the term "hemicellulose". Preferred cellulosic biomass according to the present invention comprises cotton, cotton linters and lignocellulosic biomass, i.e. biomass comprising both lignin components and cellulosic and/or hemicellulosic components.

Preferred cellulosic biomass that is particularly suited for the process according to the present invention is based on energy crops, annual plants, agricultural residues and wood.

Commercial energy crops are typically densely planted, high yielding crop species that are preferably of no or of limited value as foods. For example, wooden crops such as Salix, Miscanthus, Willow or Poplar are preferred energy crops.

Preferred examples of annual plants are straw, sugarcane and cassava.

Agricultural residues include those parts of arable crops not to be used for the primary purpose of producing food, feed or fibers, for example used animal bedding and feathers.

These residues are exemplified by bagasse from sugarcane and corn stalk.

The particularly preferred starting material of sugar cane can be divided in bagasse, sugar and straw. Bagasse is a fibrous material consisting of cellulose, hemicellulose, lignin, extractives, inorganic salts and other organic substances such as proteins and organic acids.

Bagasse and hardwood have many similarities, i.e. high xylan content, shorter fiber length and lower lignin and cellulose content compared to softwood. However bagasse has a slightly higher ash content. The ash content may be explained by differences in plant morphology and harvesting method. The short fiber length in bagasse is mainly due to its high pith content (~30%).

Overall, based on the fact that no mechanical size reduction may be needed and that higher hydrolysis yields are obtained, it is particularly preferred to conduct the process according to the present invention with non-wood agricultural residues, in particular bagasse, as the cellulosic biomass.

Wood is also a suitable material for the present process. Therein, all types of wood are suitable.

According to the present process, the cellulosic biomass pulp is enzymatically hydrolyzed. Cellulose is an insoluble linear polymer of repeating glucan units linked by β-1-4-glucosidic bonds. In water, cellulose is hydrolyzed by attack of the electrophilic hydrogen of the water molecule on the glycosidic bond. In cellulose chains each glucose unit has the potential to form three hydrogen bonds with monomers in adjacent chains, resulting in a stable crystalline structure, which is not easily hydrolysized. The rate of the hydrolysis reaction can be increased by use of elevated temperatures and pressures or can be catalyzed by dilute or concentrated acid or by enzymes, preferably, as is the case in the present invention, by enzymes.

According to a preferred embodiment of the present invention, extracellular or cell-membrane associated enzyme complexes (cellulases) that can specifically hydrolyze the cellulose polymer into soluble glucose monomers are used in the hydrolysis step. Cellulases are multi-protein complexes consisting of synergistic enzymes with different specific activities that can be divided into exo- and endo-cellulases (glucanase) and β-glucosidase (cellobiase). In addition there are enzymes (hemicelluases, laccases, lignolytic peroxidases etc.) that can break down the other main components of cellulosic biomass. All these enzymes and any combination thereof are preferred enzymes that may be used in the enzymatic hydrolysis of the present invention.

Cellobiose is a known end-product inhibitor of glucanases and β-glucosidase is known to relieve this inhibition by converting cellobiose to glucose (rate-limiting step). In industrial processes, e.g. ethanol fermentation by yeast, cellulase saccharification efficiency can be improved by simultaneouos saccharification and fermentation (SSF). The biggest challenge with SSF relates to the different temperature optima for common hydrolytic enzymes and fermenting organisms. In addition to end-product inhibition, lignin is known to reduce enzyme performance by binding non-specifically to cellulases.

It is preferred that the cellulosic biomass is subjected to at least one type of pretreatment prior to the hydrolysis, which renders at least some of the lignin of the cellulosic biomass in a water soluble form, thereby making the same particularly well suited for the hydrolysis step of the present invention.

Therefore, according to a preferred embodiment, pretreatment of the cellulose is performed to increase the specific surface area of the cellulose. Correct pretreatment has the advantages of increasing the enzyme hydrolysis rate due to more accessible substrate and also by removing potential inhibitory substances.

Although the process according to the present invention is applicable to all kinds of cellulosic materials, it is preferred that the material is pretreated in a separate step preceding the hydrolysis step. It was found that said pretreatment step increases the efficiency of enzymatic hydrolysis.

Said pretreatment is mechanical or chemical, preferably chemical.

In mechanical (pre)treatment, momentum or energy is transferred into the cellulosic biomass, for example by means of dividing or cutting or beating biomass into smaller particles. Therein, no chemical reagents are added and the chemical structure of the components of the material remains essentially unaffected.

In chemical (pre)treatment, at least one chemical reagent is added and the chemical structure of at least one component of the component in the biomass is altered. As will be discussed in more detail below, "sulfite cooking" is a chemical pretreatment and is, in fact the preferred type of pretreatment.

In a preferred embodiment, cellulosic biomass is used in the present process, in particular lignocellulosic biomass, which does not require mechanical (pre)treatment and wherein sulfite cooking is the only (pre)treatment. Sulfite cooking may be divided into four main groups: acid, acid bisulfite, weak alkaline and alkaline sulfite pulping.

In the preferred pretreatment in accordance with the present invention, the cellulosic biomass is cooked with a sulfite, preferably a sodium, calcium, ammonium or magnesium sulfite under acidic, neutral or basic conditions. This pretreatment step dissolves most of the lignin as sulfonated lignin (lignosulfonate) together with parts of the hemicellulose.

Surprisingly, in the present process, it was found that the use of sulfite cooking as a pretreatment step in the production of fuels or chemicals from fermentable sugars is very efficient as it leads to higher overall yields of chemicals. In essence, a higher output (>80%) of useful chemicals is achieved than in any other known sugar-platform biorefinery technology.

The fact that the cellulose pulp resulting from the one-step pretreatment is particularly low in impurities, in particular lignin, makes it easier to develop or adapt enzymes for the hydrolysis.

The sulfite pretreatment is preferably performed according to one of the following embodiments. Therein and throughout the present disclosure, the "sulfite pretreatment" is also referred to as "cook":

acidic cook (preferably $SO_2$ with a hydroxide, further preferably with $Ca(OH)_2$, NaOH, $NH_4OH$ or $Mg(OH)_2$), bisulfite cook (preferably $SO_2$ with a hydroxide, further preferably with NaOH, $NH_4OH$ or $Mg(OH)_2$), weak alkaline cook (preferably $Na_2SO_3$, further preferably with $Na_2CO_3$) and alkaline cook (preferably $Na_2SO_3$ with a hydroxide, further preferably with NaOH).

In regard to the sulfite pretreatment step (sulfite cooking), which is a preferred pretreatment to be implemented prior to the enzymatic hydrolysis in accordance with the present invention, the respective disclosure of WO 2010/078930 with the title "Lignocellulosic Biomass Conversion" as filed on Dec. 16, 2009 is incorporated by reference into the present disclosure.

The present invention also relates to an integrated process for the production of monosaccharides, sugar based chemicals, biofuels or materials together with sulfonated lignin from lignocellulosic biomass comprising at least the following steps:

(i) pretreatment of a lignocellulosic biomass, preferably in a sulfite cooking step;

(ii) separation of the pretreated lignocellulosic biomass from step (i) into
  (a) a liquid "spent sulfite liquor" phase, preferably comprising 50% or more of the lignin of the lignocellulosic biomass in the form of sulfonated lignin, and into
  (b) a pulp, preferably comprising 70% or more of the cellulose of the lignocellulosic biomass;

(iii) hydrolysis of the pulp (b) from step (ii) into a sugar chemistry platform comprising monosaccharides; wherein said hydrolysis step is the process for the continuous hydrolysis of lignocellulosic biomass as described above.

(iv) optionally further processing of the monosaccharides from step (iii) resulting in useful chemicals, biofuels and/or proteins; and (v) direct conversion or further processing of the sulfonated lignin of the liquid phase (a) from step (ii) into useful chemicals, biofuels and/or materials.

Figure 5:
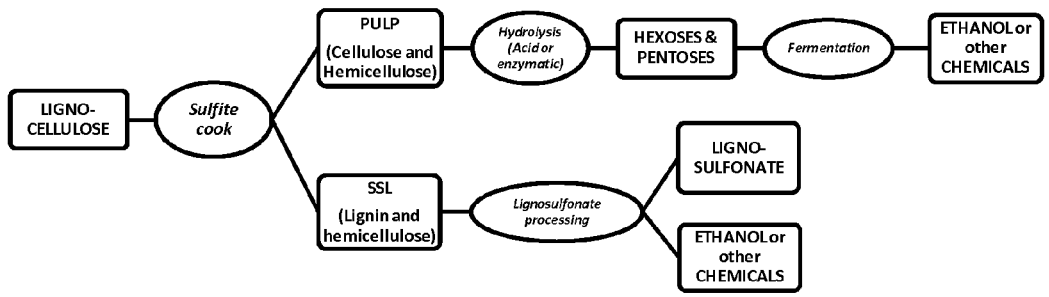
FIG. 5 is a flow sheet of an overall biorefinery concept in accordance with one embodiment of the present invention.

This overall process is schematically depicted in FIG. 5.

Step (iv) of the said process relates to the fermentation of monosaccharides, in particular of hexoses and pentoses to ethanol or other sugar based chemicals or to produce biomass proteins.

Fermentation involves microorganisms that break down sugars releasing energy while the process results in products like an alcohol or an acid. Saccharomyces cerevisiae (Bakers yeast) is most frequently used to ferment hexoses to ethanol. One mole of glucose will stoichiometrically yield 2 moles of ethanol plus 2 moles of carbon dioxide. Bagasse pulp contains relatively large amounts of pentoses. These sugars can also be either fermented or metabolized to produce biomass proteins.

With or without reference to the above described integrated process for the production of monosaccharides, the present invention relates to the hydrolysis of cellulosic biomass as described above. In regard to said hydrolysis, the following embodiments are preferred.

In a preferred embodiment, in the continuous process of the present invention, the entire slurry of liquid and solid components moves through the reactors at the same rate, i.e. unhydrolyzed fiber solids and the aqueous phase of the slurry are retained for the same time interval in said reactor.

According to a first embodiment, as exemplified in FIG. 1, the substrate, i.e. the cellulosic biomass, is fed into a reactor and enzymes are added. The process is run continuously, i.e. in a steady state. In said reactor, the substrate, i.e. the cellulosic biomass, is hydrolyzed. The viscosity of the partially hydrolyzed cellulosic biomass, in a reactor operated in accordance with the present invention, with 25% TS (comprised of 10% TSS and 15% TDS) can be approximated by the viscosity in the corresponding batch experiment after a reaction time of 16 hours.

No restrictions exist in regard to the reactor needed to run the process although a CSTR (continually stirred tank reactor) is preferred.

According to a preferred embodiment, also shown in FIG. 1, a cascade of reactors is provided to improve the glucose yield. In the additional reactors (subsequent to the first reactor described above), the substrate is further hydrolyzed resulting in a hydrolysate with high sugar concentration (=high total dissolved solids, "TDS") and a solid residue consisting of material which can not be hydrolyzed (lignin, inorganic materials, etc.).

Even though the reactor is fed with substrate having a high solid content, for example a 25% TS, the total suspended contents ("TSS") in the reactor is only about 10% at steady state (assuming 3 reactors in series with a total reaction time of 48 hours, 16 h in each reactor). The viscosity of the solution with 25% TS (comprised of 10% TSS and 15% TDS) in the steady state reactor of the present invention corresponds to the viscosity in a batch reactor after a reaction time of 16 hours or less.

The average retention time in the reactor for cellulosic biomass added to a hydrolysis reactor should be at about, preferably somewhat greater than the time required for liquefaction in a batch reactor with good stirring. Therefore, the average retention time of the first reactor should be chosen such that sufficient liquefaction is achieved for the slurry to be pumpable.

According to a second embodiment, the enzyme costs are lowered by employing enzyme recycling. The process is schematically described in FIG. 2.

In a preferred aspect of the present invention, the amount of enzymes required in the overall process is reduced by at least 30%, preferably at least 40% by means of including a recycling loop, in which the enzymes are recycled.

According to this preferred embodiment, the hydrolysate, i.e. the liquid phase comprising the hydrolyzed cellulose and enzymes, from the (last) reactor is subjected to a separation step, wherein the non-hydrolyzed solids are at least partially separated from the hydrolysate still containing enzymes. Said liquid hydrolysate is then mixed with non-hydrolyzed ("fresh") cellulosic biomass, which is then introduced into the reactor for hydrolysis.

Figure 2:
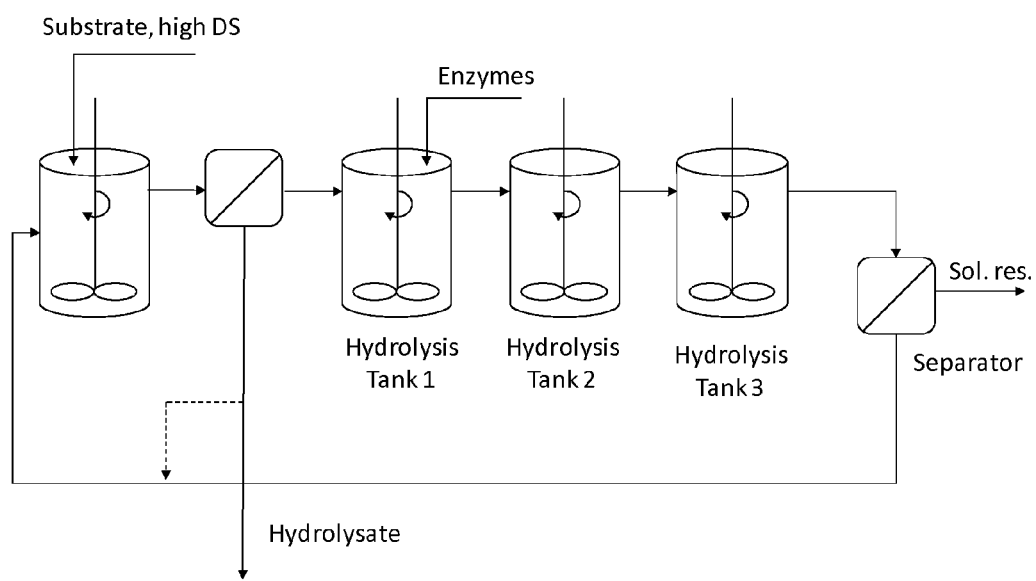
FIG. 2 shows a flow diagram of the continuous enzymatic hydrolysis of cellulosic biomass in a cascade of at least two reactors, wherein at least a portion of the enzymes added to the reactor are recycled.

This is illustrated in FIG. 2. Therein, after hydrolysis tank 3 of a cascade of three hydrolysis reactors, the hydrolysate (including enzymes) is separated from the non-hydrolyzed solid residues. Said hydrolysate is recycled into the system via a mixing tank (leftmost tank in FIG. 2). In said mixing tank, some (residual) hydrolysis might take place, but said reactor is primarily intended for mixing the recycled hydrolysate containing the enzymes with added cellulosic biomass ("substrate"). In an optional separation step after said dedicated mixing tank, some of the hydrolysate, in particular some of the final product of sugars may be separated for further processing.

Therefore, according to a preferred embodiment, at least some of the at least partially hydrolyzed cellulosic biomass that is continually removed from the reactor, preferably from the last reactor of a cascade of two or more reactors, is subjected to a separation step, wherein the non-hydrolyzed solids are at least partially separated from the hydrolysate, i.e. the liquid phase comprising hydrolyzed cellulosic biomass and enzymes, wherein said liquid hydrolysate is then mixed with cellulosic biomass, preferably in a dedicated reactor or tank, which is then introduced into the process according to the present invention.

The added advantage with this process solution is that the hydrolysate/sugar solution (after separation of non hydrolyzed material) is mixed with the substrate before the (first) reaction tank. This will decrease the amounts of enzymes needed drastically, at least 40% (due to substitution of the liquid phase in the pulp).

By mixing the hydrolysate (after separation of the unhydrolyzed solids) with fresh substrate (i.e. cellulosic biomass), the enzymes with a carbohydrate binding moiety may bind to the substrate (cellulose) before it is fed to the first hydrolysis reactor. This will allow for a further reduction in the enzyme consumption, in addition to the 40% reduction mentioned above.

In accordance with a further preferred embodiment, hydrolysis inhibition based on a sugar content that is too high (high TDS) is tackled.

Therein, any potential sugar induced inhibition of the hydrolysis is preferably overcome by sequential separation of sugars.

Figure 3:
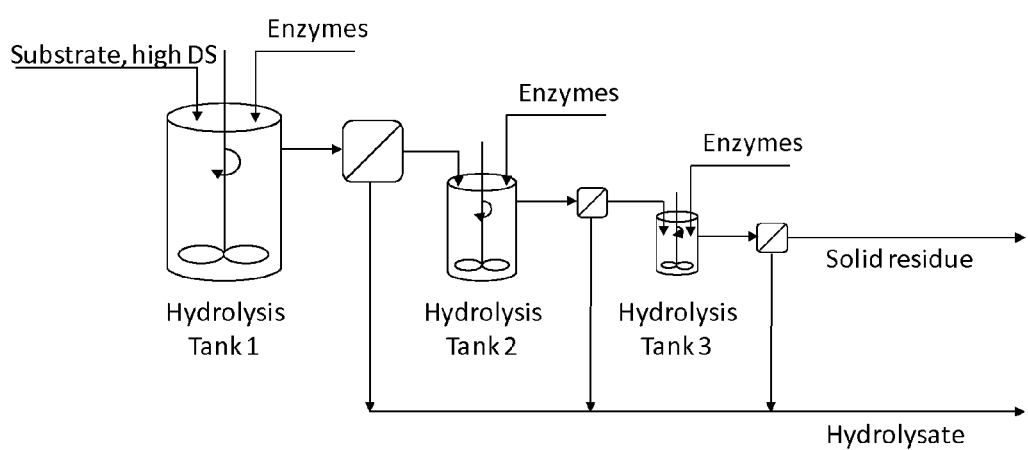
FIG. 3 shows a flow diagram of the continuous enzymatic hydrolysis of cellulosic biomass in a cascade of at least two reactors, wherein inhibition of hydrolysis by high sugar load is minimized in a cascade of reactors, which sequentially decrease in volume.

According to this preferred embodiment, as illustrated in FIG. 3, the suspended solids are separated from the liquid after the first reactor, in which a hydrolysis reaction takes place.

Typically, approximately a 60% conversion of cellulose/hemicellulose to mono sugars can be achieved in the hydrolysis reactor operated in the steady state in accordance with the present invention. The remaining 40% of non-hydrolyzed fibers is then transferred to a second reactor. It is expected that enzymes with a carbohydrate binding moiety will bind to the non-hydrolyzed fibers. Furthermore enzymes dissolved in the liquid entrained in the fibers will also be transferred to the second reactor. In addition to the enzymes that are recovered from the first reactor, a small amount of enzymes is preferably added in the second reactor.

Preferably, the size of the second hydrolysis reactor is scaled down to comply with the amount of non hydrolyzed fibers as to achieve the same or at least a similar TSS as in the first reactor.

The whole process can be repeated in the same manner for any subsequent hydrolysis reactor, which is then proportionally scaled down.

Overall, in accordance with this preferred embodiment, in the process according to the present invention, a cascade of two or more reactors for hydrolysis is used, wherein at least some of the hydrolysate, i.e. the liquid phase comprising hydrolyzed cellulosic biomass and enzymes from the first reactor is separated from the solid phase and is subjected to further processing in any of the subsequent reactors, and wherein said solid phase is added to a subsequent reactor, preferably being smaller in size and/or volume than the first reactor, wherein an additional predetermined amount of enzyme may be added to said subsequent reactor.

EXAMPLES

The following conventions as applied also throughout the specification apply for the examples:

Temperature is given in ° C.

% denotes weight % if not specified otherwise

Glucose equivalent=The amount of glucose derivable from the cellulose in the substrate Xylose equivalent=The amount of xylose derivable from the xylan in the substrate

Example 1

Figure 4:
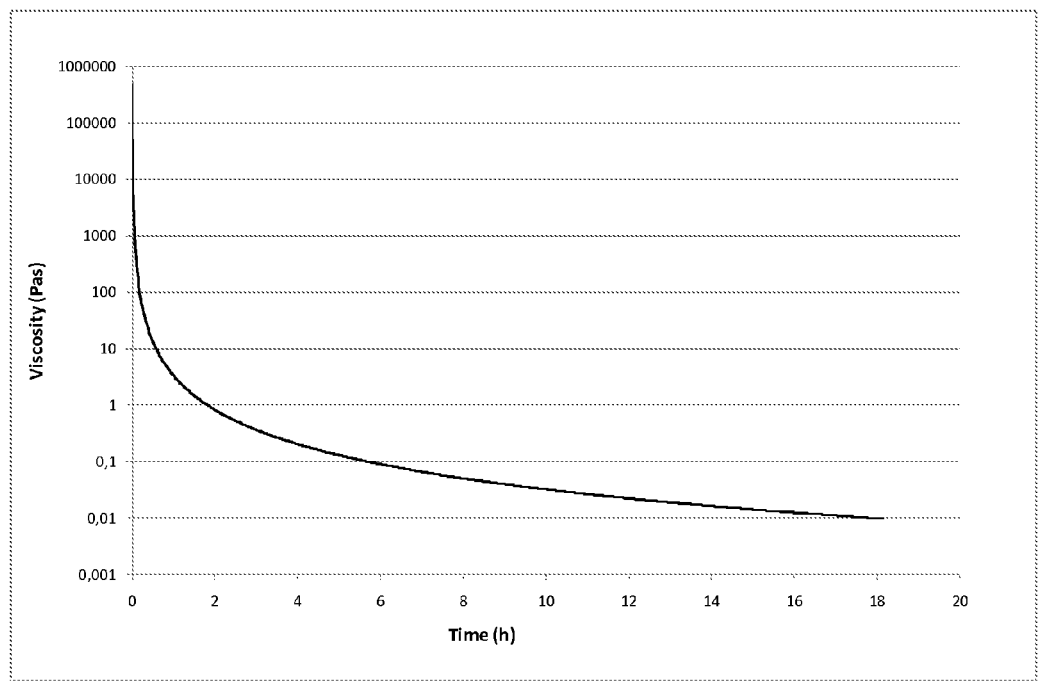
FIG. 4 depicts the development of the viscosity of cellulosic biomass subjected to enzymatic hydrolysis over time, providing information on the expected minimum retention time in the steady state.

To determine the approximate average retention time of a first reactor, one sample of alkaline sulfite cooked bagasse substrate prepared similarly to conditions described in Example 1 of WO 2010/078930 was hydrolyzed. The hydrolysis was conducted in a Physica MCR 101 rheometer in a cup with a stirrer (FL 100/6 W). The rotational speed was 30 rpm and temperature 50° C. The cellulosic biomass concentration was 10% and the enzyme addition was 40% V/w of Accellerase Duet (Genencor, Calif., USA). The viscosity was continuously monitored and the viscosity as a function of time is shown in FIG. 4.

The hydrolysis results in an initial rapid decrease in viscosity and, after a short period of time, the viscosity curve starts to flatten out and reaches a level where the sample can be seen as a liquid or liquid-like. This viscosity is dependent on the substrate (here: cellulosic biomass) and the experimental conditions, but the hydrolyzed material can be considered to be liquefied when the viscosity is lower than 3 Pas (Pascal second), i.e. lower than 3000 centipoise.

The minimum average retention time of the (first) reactor is determined by the time for liquefaction which in turn is dependent on several parameters, such as substrate, substrate concentration, and amount and type of enzymes.

Example 2

Figure 6:
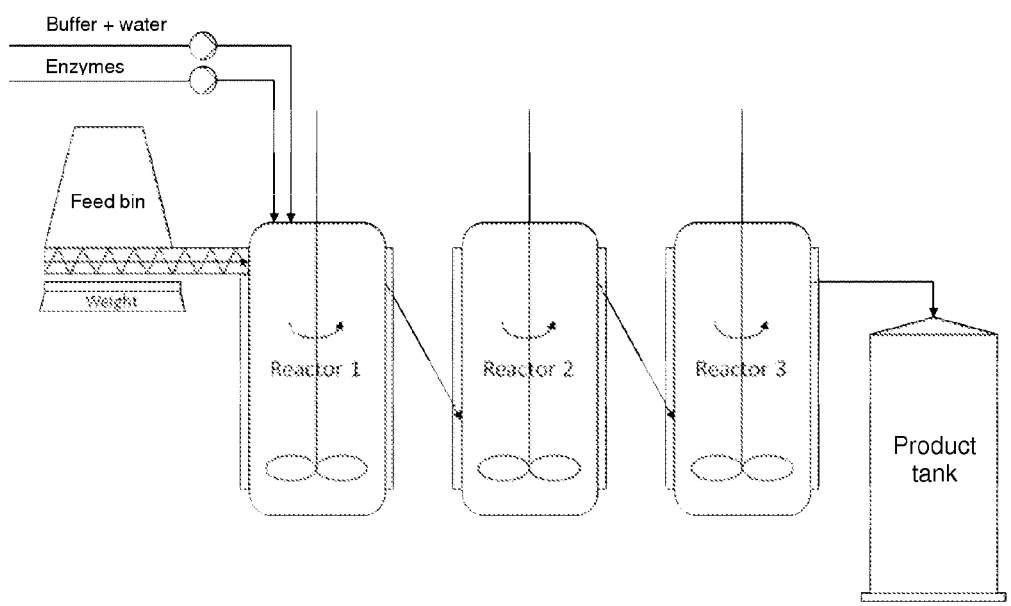
FIG. 6 shows a flow diagram of the continuous enzymatic hydrolysis of cellulosic biomass in a cascade of three reactors in accordance with Examples 2 and 3.

A sample of acid sulfite cooked bagasse substrate (bagasse pulp), prepared under similar conditions as described in Example 2 of WO 2010/078930, was subjected to continuous hydrolysis in an experimental set-up with 3 reactors in series as depicted in FIG. 6. The total volume of the system was measured to be approximately 6.6 liters. The reactors were mantled and connected to a water bath for temperature control, and cooling water was circulated in the lids to minimize evaporation from the reactors.

Enzymes (Accellerase DUET from Genencor, Calif., USA), buffer (Sodium acetate buffer, 50 mM concentration in the reactors at steady state) and the bagasse pulp were continuously added to reactor 1. The reaction mixture was kept at 50° C. in reactors 1 to 3. The hydrolysate was collected in the product tank that was water cooled to about 5° C.

The average total input to the system was 144.2 g/h. The average dry substrate concentration in the input was 17.1% and the average enzyme load was 0.273 g Accelerase DUET/g dry substrate. The average hydrolysis (retention) time was calculated to be 46 h, assuming a reaction mixture density of 1.0 g/mL.

The output from the system to the product tank was weighed regularly. The output was on average 5.1% lower than the input to the system. The main reason for the loss is assumed to be evaporation of water from the three reactors and/or accumulation of material in the reactors. Samples were taken from all three reactors twice a day to measure glucose and xylose yields. After 4-5 days the glucose and xylose values in the three reactors stabilized, thereby indicating that steady state conditions were reached. The glucose yields were calculated as (g glucose output/h)/(g glucose equivalents input/h). The glucose yields in the three reactors calculated as average values over three days at steady state were 24.6% (reactor 1), 40.2% (reactor 2) and 49.6% (reactor 3). The xylose yields were calculated as (g xylose output/h)/(g xylose equivalents input/h). The xylose yields in the three reactors calculated as average values over three days at steady state were 33.7% (reactor 1), 56.0% (reactor 2) and 66.0% (reactor 3). The viscosity was measured using a Physica MCR 101 rheometer equipped with a cup with a stirrer (FL 100/6 W), the rotational speed was 1 rpm and the temperature was 50° C. An average value of the viscosity in reactor 1 at steady state was 1.7 Pas (Pascal seconds) to be compared to the viscosity of the input (a 17.1% substrate suspension) that was measured to be 82.2 Pas.

This example shows that a continuous hydrolysis process at high solids loads at steady state produces a hydrolysate with very high glucose and xylose yields using only conventional stirring. The viscosity in the first reactor was substantially lower than that of the feed at steady state.

Example 3

A sample of alkaline sulfite cooked bagasse substrate (bagasse pulp) prepared under similar conditions as the ones described in Example 1 of WO 2010/078930 was subjected to hydrolysis in an experimental set-up with 3 reactors in series as depicted in FIG. 6. The total volume of the system was measured to be approximately 6.6 liters. The reactors were mantled and connected to a water bath for temperature control, and cooling water was circulated in the lids to minimize evaporation from the reactors.

Enzymes (Accellerase DUET from Genencor, Calif., USA), buffer (Sodium acetate buffer, 50 mM concentration in the reactors at steady state) and the bagasse pulp were continuously added to reactor 1. The reaction mixture was kept at 50° C. in reactors 1 to 3. The hydrolysate was collected in the product tank that was water cooled to about 5° C.

The average total input to the system was 144.1 g/h The average dry substrate concentration in the input was 18.8% and the average enzyme load was 0.173 g Accelerase DUET/g dry substrate The average hydrolysis (retention) time was calculated to be 46 h, assuming a reaction mixture density of 1.0 g/mL.

The output from the system to the product tank was weighed regularly. The output was on average 1% lower than the input to the system. The main reason for the loss is assumed to be evaporation of water from the three reactors and/or accumulation of material in the reactors. Samples were taken from all three reactors twice a day to measure glucose and xylose yields. After 4-5 days the glucose and xylose values in the three reactors stabilized, thereby indicating that steady state conditions were reached. The glucose yield calculated as (g glucose output/h)/(g glucose equivalents input/ h). The glucose yields in the three reactors calculated as average values over three days at steady state were 39.8% (reactor 1), 55.0% (reactor 2) and 58.8% (reactor 3). The xylose yields were calculated as (g xylose output/h)/(g xylose equivalents input/h). The xylose yields in the three reactors calculated as average values over three days at steady state were 75.0% (reactor 1), 93.2% (reactor 2) and 89.6% (reactor 3). The viscosity was measured using a Physica MCR 101 rheometer equipped with a cup with a stirrer (FL 100/6 W), the rotational speed was 30 rpm and the temperature was 50° C. An average value of the viscosity in reactor 1 at steady state was 1.5 Pas (Pascal seconds) to be compared to the viscosity of a simulated input (a 10% substrate suspension instead of 18.8% substrate suspension had to be used because of the very high viscosity) that was measured to be 249 Pas.

This example shows that a continuous hydrolysis process based on a different substrate at high solids loading at steady state produces a hydrolysate with very high glucose and xylose yields using only conventional stirring. The viscosity in the first reactor was substantially lower than that of the feed at steady state.

The invention claimed is:
1. A process for the continuous enzymatic hydrolysis of cellulosic biomass comprising at least the following steps:
(P) providing at least one reactor, which can be operated at steady state;
(A) adding cellulosic biomass to said reactor, wherein said cellulosic biomass has a solid content of at least 10% by weight;
(A') adding enzymes to said reactor;
(E) performing at least a partial enzymatic hydrolysis of the cellulosic biomass in said reactor to produce at least partially hydrolyzed cellulosic biomass comprising i) a hydrolysate comprising hydrolyzed cellulosic biomass and enzymes, and ii) a solid phase comprising non-hydrolyzed solids; wherein said at least partially hydrolyzed cellulosic biomass comprises monosaccharides,
wherein a steady state is achieved in said process, in which cellulosic biomass is continually added to said reactor, while at least partially hydrolyzed cellulosic biomass is continually removed from said reactor, wherein said at least partially hydrolyzed cellulosic biomass that is continually removed has a viscosity, as measured in a Physica MCR 101 rheometer in a cup with a stirrer at a rotational speed of 30 rpm at 50° C. temperature, of not more than 25 Pa·s (Pascal seconds); wherein in said steady state, said viscosity remains essentially constant over the course of 2 hours or more, and the concentration of said monosaccharides remains essentially constant over the course of 2 hours or more.

2. The process according to claim 1, wherein a cascade of at least two reactors comprising a first reactor and a second reactor is provided in step (P), wherein steps (A), (A'), and (E) are carried out in said first reactor.

3. The process according to claim 1, wherein the solid content of the cellulosic biomass, which is added to said reactor is at least 15% by weight.

4. The process according to claim 1, wherein the viscosity of the continually removed partially hydrolyzed cellulosic biomass as measured in a Physica MCR 101 rheometer in a cup with a stirrer at a rotational speed of 30 rpm at 50° C. temperature, is not more than 10 Pa·s.

5. The process according to claim 1, wherein the cellulosic biomass is lignocellulosic biomass.

6. The process according to claim 1, wherein the cellulosic biomass comprises more than 20% by weight cellulose.

7. The process according to claim 1, wherein the cellulosic biomass is subjected to a pretreatment prior to said hydrolysis.

8. The process according to claim 1, wherein the reactor is a CSTR, i.e. a continuously stirred tank reactor.

9. The process according to claim 1, wherein said enzymes are extracellular or cell-membrane associated enzymes complexes, that can-specifically hydrolyze the cellulose polymer into soluble glucose monomers.

10. The process according to claim 9 wherein the enzymes comprise cellulases, hemicellulases and/or β-glucosidases.

11. The process according to claim 1, wherein at least some of the at least partially hydrolyzed cellulosic biomass that is continually removed from the reactor is subjected to a separation step, wherein the non-hydrolyzed solids are at least partially separated from at least part of the hydrolysate, i.e. the liquid phase comprising hydrolyzed cellulosic biomass and enzymes, and wherein said liquid hydrolysate is then mixed with cellulosic biomass, which is then introduced into the process.

12. The process according to claim 2, wherein at least some of the hydrolysate, i.e. the liquid phase comprising hydrolyzed cellulosic biomass and enzymes, from the first reactor is separated from the solid phase and is subjected to further processing, and wherein said solid phase from said separation is added to said second reactor being smaller in size and/or volume than the first reactor, and wherein an additional amount of enzymes is added to said second reactor.

13. The process according to claim 12, which is repeated for any subsequent pair of adjacent reactors in a cascade of three or more reactors for hydrolysis, and wherein each following reactor is smaller in size and/or volume than each preceding reactor, respectively.

14. The process according to claim 2, additionally comprising the following steps:
(T) continually removing partially hydrolyzed cellulosic biomass from step (E), which has a viscosity, as measured in a Physica MCR 101 rheometer in a cup with a stirrer at a rotational speed of 30 rpm at 50° C. temperature, of not more than 25 Pa·s (Pascal seconds), from said first reactor and transferring the same into said second reactor, which is operated at steady state;
(E') performing further enzymatic hydrolysis on the partially hydrolyzed cellulosic biomass from step (E) in said second reactor.

15. The process according to claim 1, wherein the solid content of the cellulosic biomass, which is added to said reactor is at least 20% by weight.

16. The process according to claim 1, wherein the solid content of the cellulosic biomass, which is added to said reactor is at least 25% by weight.

17. The process according to claim 1, wherein the solid content of the cellulosic biomass, which is added to said reactor is at least 30% by weight.

18. The process according to claim 1, wherein the solid content of the cellulosic biomass, which is added to said reactor is 10% by weight to 45% by weight.

19. The process according to claim 1, wherein the solid content of the cellulosic biomass, which is added to said reactor is 15% by weight to 45% by weight.

20. The process according to claim 1, wherein the solid content of the cellulosic biomass, which is added to said reactor is 20% by weight to 40% by weight.

21. The process according to claim 1, wherein the solid content of the cellulosic biomass, which is added to said reactor is 15% by weight to 30% by weight.

22. The process according to claim 1, wherein the viscosity of the continually removed partly hydrolyzed cellulosic biomass as measured in a Physica MCR 101 rheometer in a cup with a stirrer at a rotational speed of 30 rpm at 50° C. temperature, is not more than 5 Pa·s.

23. The process according to claim 1, wherein the viscosity of the continually removed partly hydrolyzed cellulosic biomass as measured in a Physica MCR 101 rheometer in a cup with a stirrer at a rotational speed of 30 rpm at 50° C. temperature, is not more than 3 Pa·s.

24. The process according to claim 1, wherein the viscosity of the continually removed partly hydrolyzed cellulosic biomass as measured in a Physica MCR 101 rheometer in a cup with a stirrer at a rotational speed of 30 rpm at 50° C. temperature, is not more than 1 Pa·s.

25. The process according to claim 5, wherein said lignocellulosic biomass comprises wood, annual plants, agricultural residues or waste.

26. The process according to claim 5, wherein said lignocellulosic biomass comprises bagasse or energy crops.

27. The process according to claim 1, wherein the cellulosic biomass comprises more than 50% cellulose by weight.

28. The process according to claim 1, wherein the cellulosic biomass comprises more than 70% cellulose by weight.

29. The process according to claim 7, wherein said pretreatment is selected from: acidic cooking, bisulfite cooking, weak alkaline cooking, and alkaline cooking.

30. The process according to claim 7, wherein said cellulosic biomass is lignocellulosic biomass.

31. The process according to claim 9, wherein said extracellular or cell-membrane associated enzymes complexes comprise a mixture of cellulases and β-glucosidases.

32. The process according to claim 11, wherein after said mixing, at least some of said liquid hydrolysate is separated from said cellulosic biomass in a separation step.

\* \* \* \* \*